United States Patent
Kohara

(10) Patent No.: US 7,456,236 B2
(45) Date of Patent: Nov. 25, 2008

(54) ADHESIVE FOR PERCUTANEOUS ABSORPTION, ADHESIVE COMPOSITION FOR PERCUTANEOUS ABSORPTION AND PREPARATION FOR PERCUTANEOUS ABSORPTION

(75) Inventor: Minoru Kohara, Kyoto (JP)

(73) Assignee: Cosmed Pharmaceutical Co., Ltd., Kyoto (JP)

( * ) Notice: Subject to any disclaimer, the term of this patent is extended or adjusted under 35 U.S.C. 154(b) by 468 days.

(21) Appl. No.: 10/550,399

(22) PCT Filed: Mar. 26, 2004

(86) PCT No.: PCT/JP2004/004370

§ 371 (c)(1),
(2), (4) Date: Sep. 22, 2005

(87) PCT Pub. No.: WO2004/084946

PCT Pub. Date: Oct. 7, 2004

(65) Prior Publication Data

US 2006/0216335 A1    Sep. 28, 2006

(51) Int. Cl.
C08F 226/10 (2006.01)
(52) U.S. Cl. .................. 524/315; 524/318; 524/548; 526/263; 526/264; 424/448; 424/449
(58) Field of Classification Search .......... 524/315, 524/318, 548; 526/263, 264; 424/448, 449
See application file for complete search history.

(56) References Cited

U.S. PATENT DOCUMENTS 5,783,209 A * 7/1998 Imamura et al. ............ 424/448
6,998,432 B2 * 2/2006 Murakami et al. .......... 524/315

FOREIGN PATENT DOCUMENTS

| JP | 59-164715 A | 9/1984 |
|---|---|---|
| JP | 60-500992 A | 7/1985 |
| JP | 62-29516 A | 2/1987 |
| JP | 2-203048 | 8/1990 |
| JP | 2-232048 A | 9/1990 |
| JP | 4-150865 A | 5/1992 |
| JP | 04-272754 | 9/1992 |
| JP | 05-246752 | 9/1993 |
| JP | 07-285854 A | 10/1995 |
| JP | 8-143458 A | 6/1996 |
| WO | WO 01/68061 A1 | 9/2001 |
| WO | WO 03/014247 A1 | 2/2003 |

* cited by examiner

Primary Examiner—Bernard Lipman
(74) Attorney, Agent, or Firm—Cheng Law Group PLLC

(57) ABSTRACT

To offer adhesives for percutaneous absorption, adhesive compositions for percutaneous absorption and preparations for percutaneous absorption which show high ability to dissolve drugs and to dissolve absorption promoting agents and enable high percutaneous absorption and have suitable cohesion and adhesion and do not damage the skin when detached.

Adhesives for percutaneous absorption which comprise a copolymer in which the constituents are methoxyethyl acrylate 40-60 wt %, lauryl(meth)acrylate 30-40 wt % and a polar monomer 10-25 wt % only.

8 Claims, 2 Drawing Sheets

ADHESIVE FOR PERCUTANEOUS ABSORPTION, ADHESIVE COMPOSITION FOR PERCUTANEOUS ABSORPTION AND PREPARATION FOR PERCUTANEOUS ABSORPTION

BACKGROUND OF THE INVENTION (1) Field of the Invention

The present invention relates to adhesives for percutaneous absorption adhesive compositions for percutaneous absorption and preparations for percutaneous absorption, used in order to administer a drug through the skin continuously over along period.

(2) Description of the Related Art

In recent years various preparations such as patches and tapes for external use attached to the surface of the skin have been developed as preparations for percutaneous absorption in order to administer drugs through the surface of the skin. In this kind of adhesive preparation, the role of the adhesive is extremely important and the adhesive is required to adhere to the skin, to permit stable sustained drug release and to show little irritation to the skin. In order for these preparations for percutaneous absorption to show these characteristics, an adhesive which permits stable drug release over a long period (3 days to a week) after attachment is important.

However, the adhesives for preparations for percutaneous absorption proposed in the prior art cannot considered suitable for long term continuous drug administration.

For example, JP2-203048 A proposes an adhesive for external use which uses a copolymer which is a copolymer formed from an alkyl ester of acrylic acid or methacrylic acid at 40-80 wt %, an ethylenic unsaturated monomer containing a hydroxyl group at 10-50 wt % and an ethylenic unsaturated monomer containing a carboxyl group at 1-10 wt %, which has a glass transition temperature. (Tg) of 250K or less and a gel content after drying of 25 wt % or more. This adhesive for medical use has the disadvantage that the content in the copolymer of ethylenic unsaturated monomers having an alkoxy group is low, and therefore the saturation solubility of drugs and absorption promoters is low.

JP4-150865 A proposes an adhesive which includes a crosslinked copolymer of 99-99.9 wt % of a mixture of an acrylic acid alkyl ester and alkoxyalkyl acrylate in which the proportion of the alkoxyalkyl ester of acrylic acid at 50 wt % or less, together with a monomer containing a carboxyl group and/or hydroxyl group at 0.1-1 wt %. This adhesive is based on a (meth)acrylic acid ester, and like JP 2-232048 A above it has the drawback that the saturation solubility of drugs and absorption promoters is low.

JP 4-272754 A discloses adhesives for medical use which include more than 50% of a monomer derived from an alkoxyalkyl ester of acrylic acid which gives a homopolymer with a Tg of −35° C.; however, in this invention. Methoxyethyl acrylate is positively excluded as being unsuitable. Moreover, as the comparison examples presented below will show drugs and absorption promoters have a plasticizing effect on these adhesives, and they have the drawback that the cohesion of the adhesive composition is lowered and there are considerable adhesive residues left on the skin.

Since impregnation of drugs into the adhesive at high concentration and long-term sustained high release are important in the development of preparations for percutaneous absorption, various techniques have been proposed with the object of long-term sustained high drug release. For example, JP 5-246752 A proposes adhesives for percutaneous absorption comprising a mixture of an acrylate adhesive or silicone adhesive and Poly(Vinylpyrrolidone) as adhesives allowing the stable presence of drugs in the supersaturated state without crystallization. However, this technique is proposed in order to maintain a thermodynamically unstable state of supersaturation for a long time, and there is a considerable risk of recrystallization of the drug, limiting the efficacy thereof. Similarly; JP 6-75600 A proposes preparations for percutaneous absorption impregnated with tulobuterol in the dissolved state and the crystalline state. These preparations also have the drawback that in many cases, crystallization of the drug causes lowered adhesion of the adhesive preparation.

SUMMARY OF THE INVENTION

The object of the present invention is to offer adhesives for percutaneous absorption, adhesive compositions for percutaneous absorption and preparations for percutaneous absorption wherein drugs have high solubility and long-term release properties, and which have a suitable adhesive force and cohesive force, without causing damage to the skin when detached.

The present inventors have perfected the present invention as the result of concerted studies on optimum adhesives for continuous long-term administration of drugs, with the discovery that this object is met by adhesives for percutaneous absorption comprising a copolymer the constituents of which are methoxyethyl acrylate 40-60 wt %, lauryl(meth)acrylate 30-40 wt % and a polar monomer 10-25 wt % only with outstanding properties such as skin adhesion and drug release and low skin irritation.

DETAILED DESCRIPTION OF THE INVENTION

Figure 1:
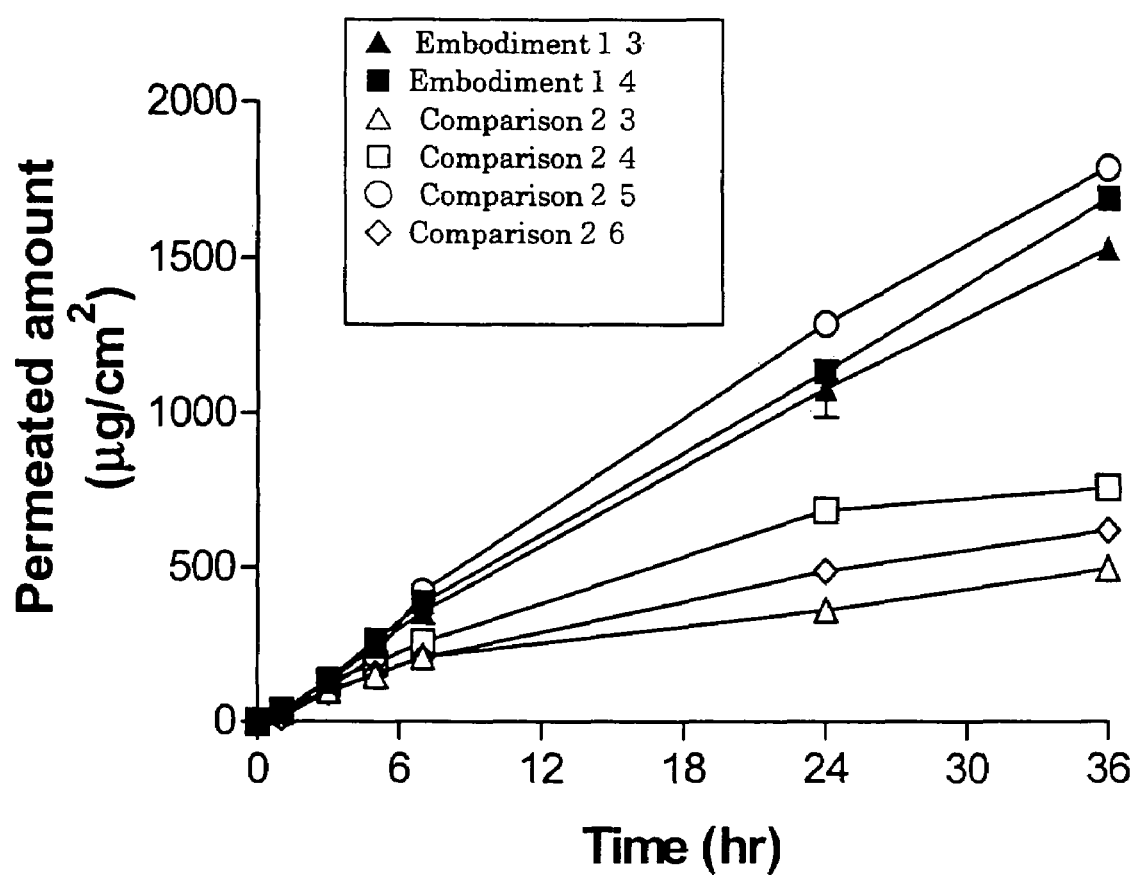
FIG. 1. A graph of the results of evaluation of ketoprofen percutaneous absorption using rat skin.

Adhesives for percutaneous absorption according to Claim 1 are characterized in as much as they comprise a copolymer in which the constituents are methoxyethyl acrylate 40-60 wt %, lauryl(meth)acrylate 30-40 wt % and a polar monomer 10-25 wt % only. The aforementioned adhesives for percutaneous absorption achieve high drug solubility by using as a monomer methoxyethyl acrylate, which is highly hydrophilic. Adhesives based on other commercially available alkoxyalkyl acrylates have been investigated, but only methoxyethyl acrylate is useful. For example, butoxyethyl acrylate has comparatively low cohesive strength in itself, and when a drug is dissolved at high concentration in an adhesive based on said monomer, or when an absorption promoter is added, it becomes plastic and cohesion is extremely decreased, so that it is not practically useful as a preparation for percutaneous absorption.

In the present invention, the proportion of methoxyethyl acrylate in the copolymer is 40-60 wt %, and preferably 45-55 wt %. When the proportion is greater than 60 wt %, gelling occurs during copolymerization and it becomes insoluble, and the viscosity of the resulting copolymer is poor. Similarly, with less than 40 wt %, the high drug solubility of methoxymethyl acrylate cannot be expressed, which is unsatisfactory for the object of the present invention.

Lauryl(meth)acrylate, which is the second monomer constituent of the aforementioned constituent of the copolymer in the present invention, needs to present at 30-40 wt %. Lauryl (meth)acrylate raises the adhesion of the adhesives according to the present invention, and also confers suitable hydrophobic characteristics on the adhesive; therefore, when combined with the principal monomer it provides suitable conditions for dissolving a wide range of drugs and absorption promoters differing in polarity.

When the proportion of lauryl(meth)acrylate in the aforementioned copolymer is 40 wt % or more, the copolymer becomes strongly hydrophobic and drug solubility is lowered. Similarly, when it is 30 wt % or less the object of conferring suitable hydrophobicity on the adhesive is inadequately achieved.

Use of 2-ethylhexyl(meth)acrylate—shorter than lauryl (meth)acrylate—as the second monomer is unsatisfactory because the capacity to dissolve hydrophobic drugs and absorption promoters (e.g. ibuprofen and isopropyl myristate) is low; and use of stearyl acrylate, with a longer alkyl chain, as the second, monomer is also unsatisfactory, because the adhesion of the copolymer is poor.

The third monomer in the copolymer in the present invention needs to be a polar monomer at 10-25 wt %. The reason for the presence thereof is that these give higher cohesion without damaging other properties, and also because they bring about crosslinking of the adhesive.

The aforementioned polar monomer is included at 10-25 wt % because less than 10 wt % is unlikely to give higher cohesion, and with more than 25% wt % the polarity of the adhesive becomes too high and the adhesive property is decreased, and it is impossible to obtain suitable adhesion. When the range is 10-25 wt % there is a good balance of cohesion and adhesion.

Examples of aforementioned polar monomers include acrylic acid, methacrylic acid, acrylamide, N-vinyl-2-pyrrolidone, N,N-dimethylacrylamide, 2-hydroxyethyl acrylate, and vinyl acetate, and these can be used singly or in combination.

The adhesives for percutaneous absorption described in Claim 2 are characterized in that the aforementioned polar monomer is one or more selected from a set comprising N-vinyl-2-pyrrolidone, acrylic acid and 2-hydroxyethyl acrylate; the adhesives for percutaneous absorption described in Claim 1 are characterized in that N-vinyl-2-pyrrolidone is an essential constituent of the aforementioned polar monomer. In addition, the adhesives for percutaneous absorption described in Claim 3 are characterized in that the content of N-vinyl-2-pyrrolidone is 5 wt % or more in the aforementioned copolymer. With such a constitution, the cohesion of the adhesive is suitably high, and the balance of cohesion and adhesion is good for an adhesive for percutaneous absorption.

The adhesive compositions for percutaneous absorption described in Claim 4 are characterized in that a drug or an added value product which is a skin cosmetic is incorporated in an adhesive for percutaneous absorption described in any of Claims 1-3.

Examples of aforementioned drugs include antipyretic and antiphlogistic drugs such as ketoprofen and piroxicam, skeletal muscle relaxants, anti-Parkinsonian drugs, antihistamines, angina, drugs for arrhythmias, antihypertensive drugs, hormones and vitamins. As the quantity of added drug, 0.05-30 wt % in the adhesive composition for percutaneous absorption is ideal in order to obtain satisfactory adhesion, cohesion and efficacy.

Examples of cosmetic added value products include whitening constituents such as ascorbyl-palmitate and oil-soluble liquorice root extract, anti-wrinkle constituents such as retinyl acetate and retinyl palmitate, constituents such as vitamin E and capsacin for promoting blood flow, and vitamins such as vitamin $D_2$, vitamin $D_3$ and vitamin K.

Adhesive compositions for percutaneous absorption described in Claim 5 are characterized in that a promoter of percutaneous absorption is further added.

Examples of aforementioned absorption promoters include fatty acid esters such as isopropyl palmitate and isopropyl myristate, glycerol esters such as glyceryl monolaurate and glyceryl monooleate, acid amides such as lauric acid diethanolamide, and neutral surfactants such as poly(ethylene glycol)dilauryl ether. These absorption promoters do not enhance the effect on percutaneous absorption if the quantity added is too small, and lower adhesion when the quantity is too great, and are ideally added at 3-40 parts by weight to 100 parts by weight of the aforementioned copolymer.

The adhesive compositions for percutaneous absorption described in Claim 6 are characterized in that the aforementioned promoter of percutaneous absorption is isopropyl myristate.

The adhesive compositions for percutaneous absorption described in Claim 7 are characterized in that the aforementioned adhesive composition for percutaneous absorption is crosslinked by a crosslinking agent.

The aforementioned crosslinking agent is added with the object of raising the cohesion of the adhesive, and examples include isocyanates and metal chelates: the quantity added is ideally 0.1-2 parts by weight to 100 parts by weight of the aforementioned copolymer. With less than 0.1 parts by weight crosslinking is weak and does not confer any improvement in cohesion; and with more than 2 parts by weight, adhesion is weakened.

The preparations for percutaneous absorption described in Claim 8 are characterized in that an adhesive ointment comprising adhesive composition for percutaneous absorption described in any of Claims 4-7 is formed on at least one side of a support.

The copolymer employed in the present invention can be obtained, for example, by free radical polymerization using 1-3 aforementioned monomers. As the polymerization processes, solution polymerization, emulsion polymerization or suspension polymerization can be employed. Solution polymerization is particularly ideal because the molecular weight distribution is comparatively narrow and there is little variation in adhesion.

In order to produce a preparation for percutaneous absorption of the present invention, an aforementioned drug or cosmetic value-added product, an absorption promoter and/or crosslinking agent, for example, can be added to an adhesive solution comprising an aforementioned copolymer and then laminated onto a detachable paper by application using a method such as a knife coater or roll coater, and then dried in an oven at a temperature of 50-100° C. for 1-10 minutes to attach an aforementioned adhesive composition to the support.

The thickness after drying of the adhesive layer so applied to the support is preferably 30-120 μm. When it is less than 30 μm the adhesion of the adhesive is weak, and when it is greater than 120 μm it is difficult to coat and dry the adhesive.

The aforementioned support can take the form of a woven fabric, nonwoven fabric, porous film or moulded film, ideally 10-100 μm thick. Woven fabric, nonwoven fabric or porous films are ideal in that they allow good passage of water vapor, whereas moulded films are good for providing a barrier to bacteria and for waterproofing.

The present invention will next be described by citing practical examples thereof; however, the present invention is not restricted to these. Except where otherwise specified, "parts" in the embodiments and comparison examples below refers to parts by weight.

EMBODIMENTS 1-3 AND COMPARISON EXAMPLES 1-8

200 g of ethyl acetate as a polymerization solvent, 0.05 g of azobisbutyronitrile as an initiator and the monomers shown in Table 1 below (grams) were loaded into a reaction vessel and the reaction vessel was purged with nitrogen, followed by polymerization for 15 hours at 70° C. The resulting copolymer solution was coated with a knife coater onto a poly (ethylene terephthalate) film to give a thickness of the dry adhesive layer of 100 μm, and then dried at a temperature of 90° C. for 15 minutes to produce adhesive sheets.

The resulting adhesive sheets were attached to the keratin layer of the shaven skin of the abdomen of Wistar rats, and detached after 24 hours, and adhesion and the state of the adhesive layer were observed with the naked eye. The results obtained are presented in Table 1.

TABLE 1

| | Monomer weight (g) | Adhesion | Cohesion |
|---|---|---|---|
| Embodiment 1 | MEA/DA/NVP/AA/HEA (43/38/6/3/10) | No detachment during 24 h | No adhesive left on the body |
| Embodiment 2 | MEA/DA/NVP/AA (48/34/15/3) | No detachment During 24 h | No adhesive left on the body |
| Embodiment 3 | MEA/DA/NVP/HEA (50/35/5/10) | No detachment during 24 h | No adhesive left on the body |
| Comparison 1 | BEA/DA/NVP/AA/HEA (43/38/6/3/10) | No detachment during 24 h | No adhesive left on the body |
| Comparison 2 | BEA/DA/NVP/AA (48/34/15/3) | No detachment during 24 h | No adhesive left on the body |
| Comparison 3 | MEA/DA/NVP/HEA (35/60/5/10) | No detachment during 24 h | No adhesive left on the body |
| Comparison 4 | MEA/DA/NVP/AA/HEA (35/50/3/2/10) | No detachment during 24 h | No adhesive left on the body |
| Comparison 5 | MEA/DA/NVP/AA (48/24/25/3) | Detached after 1 h | — |
| Comparison 6 | MEA/EHA/NVP/HEA (50/35/5/10) | No detachment during 24 h | No adhesive left on the body |
| Comparison 7 | MEA/SA/NVP/AA/HEA (43/38/6/3/10) | Detached after 2 h | — |
| Comparison 8 | MEA/DA/NVP/AA (50/45/3/2) | No detachment during 24 h | No adhesive left on the body |

MEA: Methoxyethyl acrylate
DA: Lauryl acrylate
NVP: N-vinyl 2-pyrollidone
AA: Acrylic acid
HEA: Hydroxyethyl acrylate
BEA: Butoxyethyl acrylate
EHA: 2-Ethylhexyl acrylate
SA: Stearyl acrylate
—: Not tested

EMBODIMENTS 4-6 AND COMPARISON EXAMPLES 9-16

Adhesive sheets were produced as in Embodiment 1, except that 20 parts of isopropyl myristate were added to 100 parts of the copolymer, and evaluated in the same way. The results obtained are presented in Table 2.

TABLE 2

| | Monomers, weight (g) | Adhesion | Cohesion |
|---|---|---|---|
| Embodiment 4 | MEA/DA/NVP/AA/HEA (43/38/6/3/10) | No detachment during 24 h | No adhesive left on the body |
| Embodiment 5 | MEA/DA/NVP/AA (48/34/15/3) | No detachment during 24 h | No adhesive left on the body |
| Embodiment 6 | MEA/DA/NVP/HEA (50/35/5/10) | No detachment during 24 h | No adhesive left on the body |
| Comparison 9 | BEA/DA/NVP/AA/HEA (43/38/6/3/10) | No detachment during 24 h | Adhesive left on the body |
| Comparison 10 | BEA/DA/NVP/AA (48/34/15/3) | No detachment during 24 h | Adhesive left on the body |
| Comparison 11 | MEA/DA/NVP/HEA (35/60/5/10) | No detachment during 24 h | Adhesive left on the body |
| Comparison 12 | MEA/DA/NVP/AA/HEA (35/50/3/2/10) | No detachment during 24 h | No adhesive left on the body |
| Comparison 13 | MEA/DA/NVP/AA (48/24/25/3) | No detachment during 24 h | Adhesive left on the body |
| Comparison 14 | MEA/EHA/NVP/HEA (50/35/5/10) | Detached after 1 h | — |
| Comparison 15 | MEA/SA/NVP/AA/HEA (43/38/6/3/10) | No detachment during 24 h | Adhesive left on the body |
| Comparison 16 | MEA/DA/NVP/AA (50/45/3/2) | No detachment during 24 h | Adhesive left on the body |

MEA: Methoxyethyl acrylate
DA: Lauryl acrylate
NVP: N-vinyl 2-pyrollidone
AA: Acrylic acid
HEA: Hydroxyethyl acrylate
BEA: Butoxyethyl acrylate
ERA: 2-Ethylhexyl acrylate
SA: Stearyl acrylate
—: Not tested

EMBODIMENTS 7-9

Adhesive sheets were produced as in Embodiment 1, except that 40 parts of isopropylmyristate and 0.5 part of an isocyanate crosslinking agent (Nippon Polyurethane Co., Coronate L) were added to 100 parts of the copolymer, and evaluated in the same way. The results obtained are presented in Table 3.

TABLE 3

| | Monomers, Weight (g) | Adhesion | Cohesion |
|---|---|---|---|
| Embodyment 7 | MEA/DA/NVP/AA/HEA (43/38/6/3/10) | No detachment during 24 h | No adhesive left on the body |
| Embodyment 8 | MEA/DA/NVP/AA (48/34/15/3) | No detachment during 24 h | No adhesive left on the body |
| Embodyment 9 | MEA/DA/NVP/HEA (50/35/5/10) | No detachment during 24 h | No adhesive left on the body |

MEA: methoxyethyl acrylate
DA: Lauryl acrylate
NVP: N-vinylpyrrolidone
AA: acrylic acid
HEA: hydroxyethyl acrylate

EMBODIMENTS 10-12 AND COMPARISON EXAMPLE 17-22

The copolymers obtained in embodiments (1-3) and comparison examples (1-4, 6 and 8) were used in testing for drug solubility in adhesives comprising different copolymers, using felbinac as the drug.

Felbinac was added to each of the copolymer solutions to give 2, 4 or 8%, made into a rolled sheet and the solvent was removed by heating at 90° C. for 10 minutes. The resulting adhesives containing the drug were stored at room temperature for 4 weeks, and the presence or absence of crystals was observed.

The results are presented in Table 4.

TABLE 4

| Examples Comparison | Adhesive used | Felbinac (%) 2 | 4 | 8 | Nature of the drug-containing sheet |
|---|---|---|---|---|---|
| Embodyment 10 | Embodyment 1 | ○ | ○ | ○ | Good adhesion and cohesion |
| Embodyment 11 | Embodyment 2 | ○ | ○ | ○ | Good adhesion and cohesion |
| Embodyment 12 | Embodyment 3 | ○ | ○ | ○ | Good adhesion and cohesion |
| Comparison 17 | Comparison 1 | ○ | X | X | Poor cohesion. Adhesive of 4, 8% felbicac sheet left on the skin |
| Comparison 18 | Comparison 2 | ○ | X | X | Poor cohesion. Adhesive of 4, 8% felbicac sheet left on the skin |
| Comparison 19 | Comparison 3 | ○ | X | X | Poor cohesion. Adhesive of 4, 8% felbicac sheet left on the skin |
| Comparison 20 | Comparison 4 | ○ | X | X | Good adhesion and cohesion |
| Comparison 21 | Comparison 6 | ○ | ○ | ○ | Poor cohesion. Adhesive of 8% felbicac sheet left on the skin |
| Comparison 22 | Comparison 8 | ○ | X | X | Poor cohesion. Adhesive of 4, 8% felbicac sheet left on the skin |

○: No crystals
X: crystals

EMBODIMENTS 13-15 AND COMPARISON EXAMPLES 23-27

In Vitro Evaluation of Percutaneous Absorption of Ketoprofen and Felbinac (Preparation of Samples for In Vitro Testing of Percutaneous Absorption)

The drugs were dissolved in adhesive compositions by adding isopropyl myristate as an absorption promoter to copolymer solutions to give 20 parts per 100 parts of the adhesive constituent, to give a saturated concentration in the adhesive compositions. The drugs used were ketoprofen and felbinac. The compositions containing the dissolved drugs were coated onto poly(ethylene therephthalate) film to give a thickness when dry of 100 μm, and dried at a temperature of 90° C. for 15 minutes, to produce drug-containing adhesive sheets. The composition of the samples used in the in vitro tests is presented in Table 5.

TABLE 5

| | Adhesive used | Felbinac (%) | Nature of the drug-containing sheet |
|---|---|---|---|
| Example/Comparison | | | |
| Embodyment 13 | Embodyment 1 | 25 | Good adhesion and cohesion |
| Embodyment 14 | Embodyment 2 | 22 | Good adhesion and cohesion |
| Comparison 23 | Comparison 3 | 6 | Poor cohesion |
| Comparison 24 | Comparison 4 | 8 | Poor cohesion |
| Comparison 25 | Comparison 6 | 25 | IPM bleeding, poor adhesion |
| Comparison 26 | Comparison 8 | 8 | Poor cohesion |
| Embodyment/Comparison | | | |
| Embodyment 15 | Embodyment 1 | 6.8 | Good adhesion and cohesion |
| Embodyment 16 | Embodyment 2 | 7.0 | Good adhesion and cohesion |
| Comparison 27 | Comparison 4 | 1.2 | Good adhesion and cohesion |

(In vitro absorption tests)

Tests of permeation of rat skin were performed using the samples in Table 5 above. The tests were performed using Franz diffusion cells having a diffusion cross-sectional area of 3.14 cm$^2$ were used. As the permeation membrane, shaved abdominal skin from male Wistar rats was used, and physiological saline+polyethylene glycol 600 (80:20 v/v) was used as the receptor solution. The sample was attached to the keratin layer of the rat skin and at set times thereafter 100 ml of receptor solution was sampled, and the concentration of drug permeated through rat skin into the receptor solution was confirmed by using high-performance liquid chromatography (HPLC).

(HPLC Conditions)

Column: ODS reverse-phase partition column

Mobile phase: Ketoprofen—phosphate buffer (pH 3.0)+acetonitrile (50:50 vol/vol)

Felbinac—ditto

Detection: Ketbprofen—UV 250 nm

Felbinac—ditto (Results of the In Vitro Absorption Tests)

Figure 2:
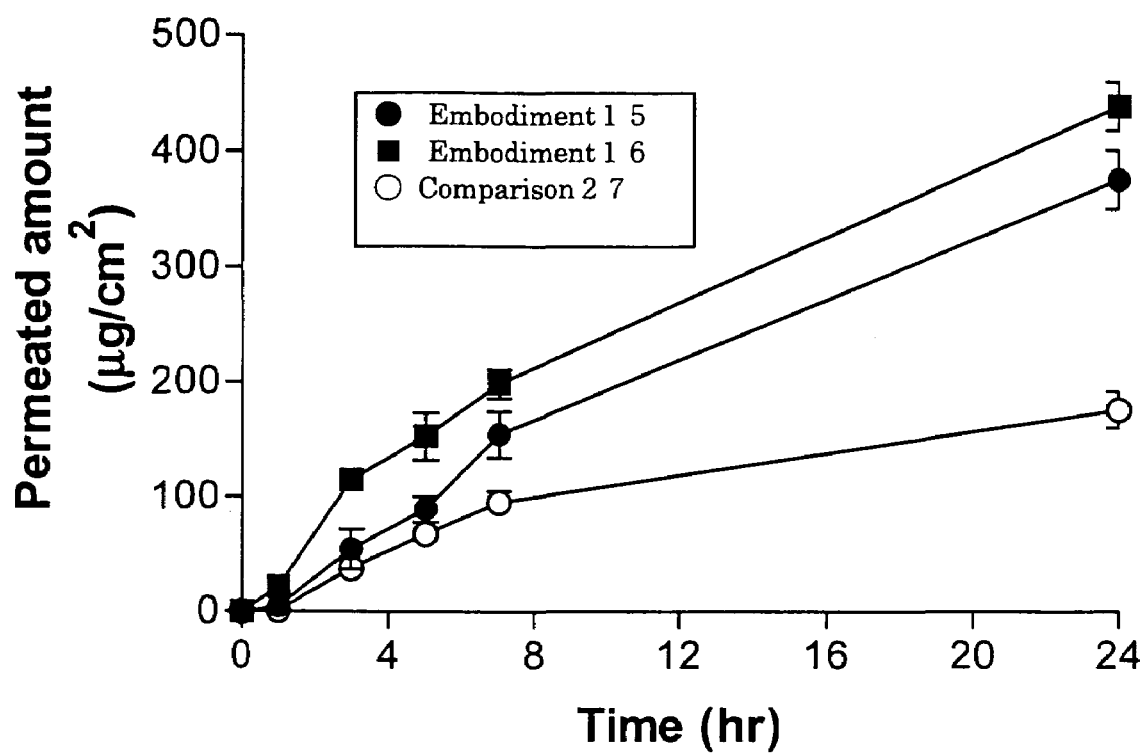
FIG. 2. A graph of the results of evaluation of felbinac percutaneous absorption using rat skin.

The results obtained are presented in FIG. 1 (ketoprofen) and FIG. 2 (felbinac).

Comparing the embodiments and comparison examples, it is evident that except for Comparison Example 25, the embodiments showed persistent percutaneous absorption for 36 hours, whereas in the case of the comparison examples absorption was virtually complete after 8 hours. This indicates that the high drug solubility shown of the copolymer adhesives shown in the embodiments results in the possibility of high release over a long period.

Comparison Example 26 showed persistent drug release over a long period but poor adhesion, precluding practical use as a preparation for percutaneous absorption.

When an adhesive for percutaneous absorption of a composition of the present invention, drugs can be impregnated into the adhesive at high concentration, making it possible to give long-term persistent percutaneous absorption and good adhesion.

The invention claimed is:

1. An adhesive for percutaneous absorption comprising a copolymer in which the constituents are methoxyethyl acrylate 40-60 wt %, lauryl(meth)acrylate 30-40 wt %, and a polar monomer 10-25 wt % only,
   wherein said polar monomer comprises N-vinyl-2-Pyrrolidone.

2. The adhesive for percutaneous absorption as described in claim 1, wherein said polar monomer further comprises one or more selected from a set comprising acrylic acid and 2-hydroxyethyl acrylate.

3. The adhesive for percutaneous absorption as described in claim 1, wherein N-vinyl-2-Pyrrolidone is in an amount of 5 wt % or more in said copolymer.

4. An adhesive composition for percutaneous absorption comprising a drug or a value-added cosmetic substance for the skin in the adhesive for percutaneous absorption described in any one of claims 1, 2 and 3.

5. The adhesive composition for percutaneous absorption as described in claim 4, further comprising a promoter of percutaneous absorption.

6. The adhesive composition for percutaneous absorption as described in claim 5, wherein said promoter of percutaneous absorption is isopropyl myristate.

7. The adhesive composition for percutaneous absorption as described in claims 4, which is crosslinked by a crosslinking agent.

8. A preparation for percutaneous absorption produced by forming an adhesive ointment comprising the adhesive composition for percutaneous absorption described in claims 4 on at least one side of a support.

* * * * *